United States Patent [19]
Kelley et al.

[11] Patent Number: 5,679,154
[45] Date of Patent: *Oct. 21, 1997

[54] CYTOLOGY CENTRIFUGE APPARATUS

[75] Inventors: Thomas F. Kelley, Canton; Henry A. Petithory, Southborough; Todd W. Soares, Milford, all of Mass.

[73] Assignee: Norfolk Scientific, Inc., Norwood, Mass.

[*] Notice: The term of this patent shall not extend beyond the expiration date of Pat. No. 5,480,484.

[21] Appl. No.: 576,679

[22] Filed: Dec. 21, 1995

Related U.S. Application Data

[63] Continuation-in-part of Ser. No. 204,608, Mar. 1, 1994, Pat. No. 5,480,484.
[51] Int. Cl.$^6$ ................................................ B05C 13/00
[52] U.S. Cl. .................. 118/52; 206/456; 210/380.1; 422/72; 422/101; 422/104; 436/45; 436/46; 494/16; 494/20
[58] Field of Search .............. 118/52, 416; 427/240; 494/16, 20; 210/380.1, 361; 422/72, 101, 104; 436/45, 46; 435/312; 206/456

[56] References Cited

U.S. PATENT DOCUMENTS

| | | | |
|---|---|---|---|
| 3,577,267 | 5/1971 | Preston, Jr. et al. | 117/101 |
| 3,705,048 | 12/1972 | Staunton | 117/3 |
| 3,870,014 | 3/1975 | Buck | 118/52 |
| 4,016,828 | 4/1977 | Maher, Jr. et al. | 118/6 |
| 4,031,852 | 6/1977 | Clarke et al. | 118/52 |
| 4,037,003 | 7/1977 | Maher, Jr. et al. | 427/2 |
| 4,103,643 | 8/1978 | Staunton | 118/50 |
| 4,108,109 | 8/1978 | Barger et al. | 118/52 |
| 4,197,329 | 4/1980 | Holroyd et al. | 427/2 |
| 4,209,548 | 6/1980 | Bacus | 427/2 |
| 4,266,505 | 5/1981 | Bacus | 118/699 |
| 4,280,442 | 7/1981 | Johnson | 118/52 |
| 4,294,866 | 10/1981 | Johnson | 427/2 |

(List continued on next page.)

OTHER PUBLICATIONS

Product Literature entitled "You Can Turn Centrifuge Into The Most Effective Cytological Slide Preparation System Available", International Equipment Company, Needham Hts. MA, six unnumbered pages.

Product Literature entitled "The New Sakura AutoSmear Cytocentrifuge CF-12DE" Sakura Finetek U.S.A., Inc., one two sided page.

Product Literature entitled "The Versatile Cyto-System", Heraius Sepatech GmbH, Four unnumbered pages.

Product Literature entitled "Cytospin Cytocentrifuge Accessories", Shandon Inc., One two-sided page.

Data sheet, "Making Blood Smear Slides", The Office Laboratory, Hematology, pp. 189–191.

American Journal of Medical Technology, "Blood Sample Preparation for Automated Differential Systems", vol. 39, No. 11, pp. 435–442.

(List continued on next page.)

Primary Examiner—Laura Edwards
Attorney, Agent, or Firm—Weingarten, Schurgin, Gagnebin & Hayes LLP

[57] ABSTRACT

Removed cytology centrifuge apparatus includes single or multiple well cell concentrators for being rotated by a centrifugal spinner. A rotor is removably supported by the spinner for rotation and is adapted to receive two or four cell concentrators. The rotor supports the cell concentrators in an unrestrained manner, thereby enhancing the ease of use and flexibility of the apparatus. The cell concentrator is shaped to rest stably on a planar surface in a tilted manner so that a fluid specimen contained therein is prevented from contacting the slide prior to centrifugation. Each cell concentrator includes a chamber having at least one fluid receiving aperture and at least one fluid expulsion aperture. The chamber is secured to a backing plate by a fastening mechanism, with the slide sandwiched therebetween. In one embodiment, the chamber is hinged to the backing plate. Also described is a bibulous pad interposed between the chamber and the slide in order to absorb excess sample fluid.

20 Claims, 10 Drawing Sheets

U.S. PATENT DOCUMENTS

| | | | |
|---|---|---|---|
| 4,349,275 | 9/1982 | Ayotte et al. | 356/36 |
| 4,391,710 | 7/1983 | Gordon | 210/361 |
| 4,468,410 | 8/1984 | Zeya | 427/2 |
| 4,576,110 | 3/1986 | Wells | 118/52 |
| 4,633,804 | 1/1987 | Arii | 118/52 |
| 4,819,804 | 4/1989 | Levy | 206/456 |
| 4,853,188 | 8/1989 | Toya | 422/72 |
| 4,941,426 | 7/1990 | Sago et al. | 118/52 |
| 5,009,185 | 4/1991 | Stokes et al. | 118/52 |
| 5,252,228 | 10/1993 | Stokes et al. | 210/781 |
| 5,292,000 | 3/1994 | Levy | 206/456 |
| 5,326,398 | 7/1994 | Kelley et al. | 118/52 |
| 5,380,435 | 1/1995 | Stokes et al. | 210/361 |
| 5,466,371 | 11/1995 | Barlow et al. | 422/72 |
| 5,470,758 | 11/1995 | Hayes | 422/72 |
| 5,480,484 | 1/1996 | Kelley et al. | 118/52 |

OTHER PUBLICATIONS

Data Sheet, "Blood Film Examination".

Product Literature entitled "Introducing CYTOPRO Cytocentrifuge Making a Tough Job Easier", dated 1992, of Wescor, Inc., 459 South Main Street, Logan, Utah 84321, consisting of six unnumbered pages.

Product Literature entitled "You Can Turn Your Centrifuge Into The Most Effective Cytological Slide Preparation System Available", undated, of International Equipment Company, 300 Second Ave., Needham Hts., MA 02194, consisting of six unnumbered pages.

Product Literature entitled "The New Sakura AutoSmear Cytocentrifuge CF–12DE", undated, of Sakura Finetek U.S.A., Inc. 22828 Lockness Avenue, Torrance, California 90501, consisting of one two–sided page.

Product Literature entitled "The versatile Cyto–System", undated, of Heraeus Sepatech GmbH, P.O. Box 12 20, Am Kalkberg, D–3360 Osterode, consisting of four unnumbered pages.

Product Literature entitled "Cytospin Cytocentrifuge Accessories", undated, of Shandon Inc., 171 Industry Drive, Pittsburgh, PA 15275, consisting of one two–sided page.

Product Literature entitled "2. Operating the Cytospin 3", from Shandon Operator's Manual, dated 1987, of Shandon Inc., 171 Industry Drive, Pittsburgh, PA 15275, consisting of four pages in non–sequential order.

STATSPIN CYTOFUGE™ product literature, Jun. 1994, one page.

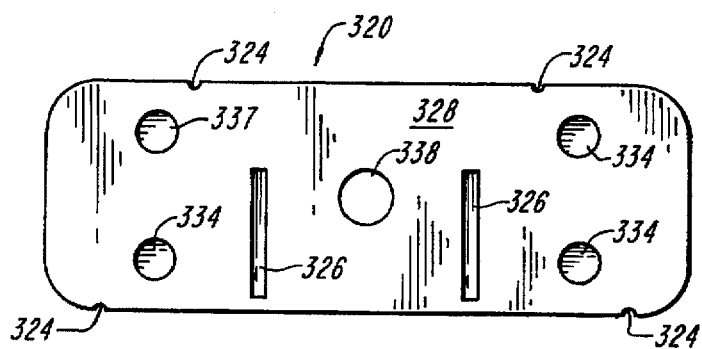
FIG. 12
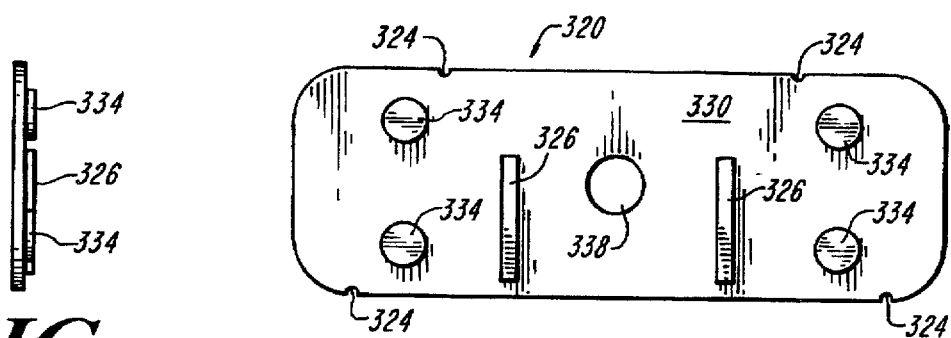
FIG. 12A  FIG. 12B
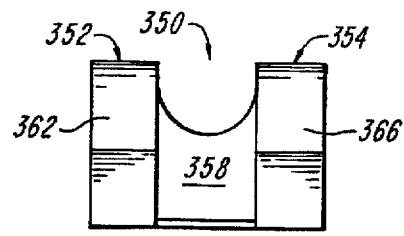
FIG. 13
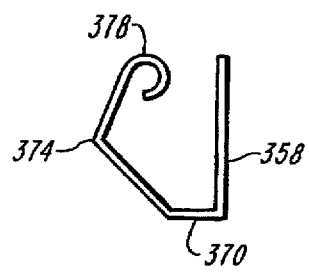  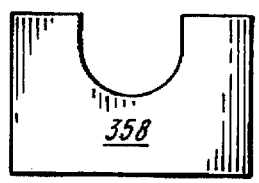
FIG. 13A  FIG. 13B

CYTOLOGY CENTRIFUGE APPARATUS

RELATED CASE INFORMATION

This patent application is a Continuation-in-Part application U.S. patent application Ser. No. 08/204,608, filed Mar. 1, 1994, entitled CYTOLOGY CENTRIFUGE APPARATUS and issued as U.S. Pat. No. 5,480,484 on Jan. 2, 1996.

FIELD OF THE INVENTION

This invention relates generally to centrifuge apparatus and more particularly, to improved cytology centrifuge apparatus.

BACKGROUND OF THE INVENTION

Centrifugation of cells suspended in a carrier fluid in order to deposit the cells on a microscope slide for subsequent analysis is known in the field of cytology. Exemplary cell suspension fluids include normal body fluids such as synovial fluid or cerebrospinal fluid, abnormal fluids such as ascites fluid resulting from a cancer, or artificial fluids such as cell cultures. During centrifugation, the carrier fluid is forced against the slide causing cells suspended therein to attach to the slide, preferably in a substantially monolayer configuration. Subsequent processing may include staining the deposited cells with staining reagents to enhance selected cell attributes prior to microscopic analysis of the cells.

Generally, centrifugation apparatus includes an electromechanical spinner for supporting a rotor and having a motor for rotating the rotor. The rotor includes a mechanism for mounting and restraining one or more sample chambers, referred to hereinafter as cell concentrators, for rotation. The cell concentrators include generally, a chamber having a fluid receiving aperture through which a fluid specimen is added and a fluid expulsion aperture through which the fluid is expelled during centrifugation, a microscope slide disposed in fluid communication with the fluid expulsion aperture, and a securing mechanism for securing the slide to the chamber.

Since some of the materials to be centrifuged may be toxic or present a biohazard, various schemes are employed to promote the safer use of centrifuges. One technique for improving the safety of the centrifugation process is to provide a removable rotor so that the cell concentrators can be mounted in the rotor, loaded with specimens and, after centrifugation, removed from the rotor in a safe environment such as in some type of biological safety cabinet.

Bibulous paper, sometimes referred to as a filter card or a bibulous pad, is often disposed between the chamber and the microscope slide and comprises a fibrous material for absorbing carrier fluid. More particularly, the bibulous paper has an aperture aligned with the fluid expulsion aperture in the chamber so that, theoretically, fluid communication between the chamber and the slide is not impaired. However, due to the location of the bibulous paper relative to the slide, the paper may absorb the carrier fluid so rapidly that cells are absorbed and lost to analysis. Moreover, the capacity and rate of absorption of carrier fluid by the bibulous paper are difficult to control and depend on such variables as the force applied by the securing mechanism which secures the chamber to the slide, the uniformity of such force, the amount of carrier fluid, and the duration of centrifugation. Another potential drawback to the use of bibulous paper interposed between the chamber and the slide is possible contamination of the deposited cells by fibers of the paper itself.

Significantly, bibulous paper has a limited fluid retention capacity. Once saturated, excess fluid in the carrier is spun off and flung at a relatively high velocity against the outside of the rotor creating potentially dangerous aerosols.

As is believed in the field of cytology centrifugation, it is desirable to keep the carrier fluid from contacting the microscope slide prior to centrifugation. Theoretically, this practice enhances the uniformity of the cell deposition and is essential where bibulous paper is inserted between the chamber and the slide since fluid contact with the bibulous paper will result in undesirable cell absorption.

SUMMARY OF THE INVENTION

In accordance with the invention, cytology centrifuge apparatus is provided with an improved single or multiple well cell concentrator. The concentrator includes a chamber having a top surface in which at least one fluid receiving aperture is disposed and a front surface in which at least one fluid expulsion aperture is disposed. Each fluid receiving aperture and fluid expulsion aperture pair defines a well of the chamber and, in the multiple well concentrator, adjacent wells are isolated by separating walls. In operation, a fluid specimen, such as a carrier fluid with cells suspended therein, is inserted into the fluid receiving aperture of each well. The associated fluid expulsion aperture permits expulsion of the fluid onto an adjacently held microscope slide during centrifugation for deposition of the cells. In one embodiment, a backing plate having protruding top and bottom edges is secured, or clamped to the chamber by a pair of clips with the slide sandwiched therebetween. The top and bottom edges of the backing plate maintain the chamber and slide in vertical alignment and the clips maintain the chamber and slide in horizontal alignment.

An electromechanical spinner is provided with a central depression, or bowl, for removably supporting a rotor for rotation. The rotor has multiple positions for receiving two or four cell concentrators in an unrestrained manner, thereby enhancing the ease of use of the apparatus. With this arrangement, the need for a mechanism for mounting and restraining the concentrators in the rotor is eliminated since the concentrators rest freely in a corresponding rotor position prior to, during, and after centrifugation.

Each cell concentrator is shaped to rest stably on a planar surface in a tilted manner. More particularly, the bottom edge of the backing plate has a beveled portion which causes the cell concentrator to rest stably in a tilted position until the concentrator is subjected to centrifugal forces during centrifugation. When a concentrator is placed unrestrained in the rotor in its tilted position prior to centrifugation, specimen fluid therein is kept away from the fluid expulsion aperture and the adjacent slide, thereby enhancing the uniformity of cell deposition on the slide.

During centrifugation, rotation of the rotor and concomitant rotation of the concentrators contained therein, causes the concentrators to pivot to a vertical orientation, with the backing plate contacting an adjacent inner sidewall of the rotor. After centrifugation, the cell concentrators automatically pivot back to their tilted positions in which carrier fluid flows away from the slide.

The rotor has a ledge around the upper perimeter thereof and a cover is provided for resting on the ledge to cover the rotor. Even if the wells of the cell concentrators are overfilled with a fluid specimen, the excess fluid will leave the chamber as soon as the concentrator begins to pivot to the vertical position and while the rotor is rotating at a relatively slow speed. Such fluid will flow to the adjacent inner sidewall of the rotor and be trapped under the ledge. With this arrangement, the formation of potentially harmful aerosols, such as may occur when fluid is flung at a high speed onto a distant surface is prevented.

The tilted position which the concentrators resume after centrifugation facilitates removal of carrier fluid by aspiration with a pipette inserted into the one or more wells through the corresponding fluid receiving aperture. The cell concentrator can be disassembled and the slide then processed by any of various fixing and staining procedures. Or, when the cell concentration of the sample fluid was very low, additional aliquots of the specimen can be added and reprocessed, or respun to increase the number of cells on the slide.

Cell staining can be achieved in the assembled concentrator. That is, once centrifugation is completed (and carrier fluid removed), staining reagents may be introduced into the one or more wells by a pipette inserted through the corresponding fluid receiving aperture. More particularly, the concentrator is first inverted so that the slide is resting in a horizontal orientation. Stain flows through the fluid expulsion aperture to contact cells attached to the slide. Use of the concentrator as a staining chamber is possible since there is no bibulous paper between the chamber and the slide which would absorb the stain. The relatively small well volume, shallow wells, and preferred fabrication of the chamber from a transparent material further facilitate use of the concentrator for staining deposited cells. The ability to stain cells in the assembled concentrator is desirable since controlled and repeatable application of staining reagents is possible, thereby minimizing waste of expensive staining reagents. Staining reagent waste is further reduced since reagent evaporation is minimized in the substantially closed concentrator.

A viewing aperture is provided in the backing plate adjacent to the at least one fluid expulsion aperture in order to permit viewing of sedimented and attached cells during the staining process from the rear surface of the slide. More particularly, the cells can be viewed during the staining process by inverting the concentrator and placing it under a conventional microscope. Alternatively, an inverted microscope may be used to eliminate the need for inverting the cell concentrator. Viewing cells during the staining process may be desirable for use in developing optimum staining processes.

In another embodiment, the cell concentrator is provided with an internal shelf in each well extending from the rear chamber surface partially toward the front chamber surface and a bibulous pad disposed below the shelf. A fluid specimen is spaced from the bibulous pad by the shelf when the chamber is tilted prior to centrifugation. After centrifugation, as the concentrator pivots back to the tilted position, carrier fluid flows past the shelf and is absorbed by the bibulous pad. This arrangement eliminates the need for aspiration of carrier fluid following centrifugation without disadvantageously absorbing cells and preventing their attachment to the slide.

The bibulous pad may comprise a single pad of substantially uniform absorbency. Alternatively, the bibulous pad may comprise a first higher absorbency pad portion and a second lower absorbency portion, with the first pad portion disposed below the shelf and the second portion disposed below the pad and extending toward the slide. With this arrangement, the second portion provides a wicking action to slowly absorb carrier fluid from the slide surface during centrifugation and to draw such fluid toward the adjacent, higher absorbency pad portion for absorption and retention. The use of separate materials for the wick and the pad allows the exact selection of material for each disparate purpose. The rate of wicking is controlled by the composition of the wick and not from poorly controlled attempts at compression of a material not at all ideal for use as a wick.

In accordance with a further embodiment of the invention, an alternate cell concentrator is provided for use with a spinner and rotor as described above. The cell concentrator includes a sample carrier, or chamber, a slide in fluid communication with the chamber, a bibulous pad interposed between the slide and chamber, a substantially planar backing plate against which the slide is urged in assembly and a securing mechanism to secure the backing plate to the chamber, with the slide and bibulous pad interposed therebetween. The chamber includes a tube with a fluid receiving aperture for receiving a fluid specimen and a fluid expulsion aperture in fluid communication with the slide. Also described is a unitary sample chamber and backing plate combination member having a sample chamber hinged to a backing plate.

The fluid expulsion aperture is bordered by a raised rim and the bibulous pad has an aperture aligned with the fluid expulsion aperture, so that, in assembly, the bibulous pad is compressed against the raised rim in order to restrict the fluid path between the chamber and the bibulous pad. The chamber has at least one locating pin protruding from its rear surface and the bibulous pad has at least one locating aperture adapted for mating with the locating pin of the chamber. With this arrangement, the bibulous pad is precisely aligned relative to the fluid expulsion aperture of the chamber.

In accordance with a further feature of the cell concentrator, the chamber has at least one locating tab extending inward from a lip along an edge portion thereof and the backing plate has at least one notch along an edge portion thereof. In assembly, the notch of the backing plate mates with the tab of the chamber to ensure the desired component alignment. Furthermore, the bibulous pad and slide are positioned within the lip of the chamber, so as to further ensure proper alignment of the bibulous pad, slide, chamber and backing plate.

The securing mechanism is a clip member having a pair of legs attached to a rear wall by a base portion. In assembly, the rear wall of the clip member contacts the rear surface of the backing plate and the legs contact the front surface of the chamber, with the legs straddling the tube. The front surface of the chamber has a pair of substantially parallel ridges protruding therefrom which form a detent. Each of the clip member legs has a rounded end portion which is positioned in the detent, between the pair of ridges, in assembly. A pair of guide rails protrude from the rear surface of the backing plate and provided a mechanism for aligning the fastener with the backing plate. Alternatively, the backing plate includes a recess for aligning the fastener. These features ensure that the clip member is precisely and reproducibly positioned relative to the chamber and backing plate, so as to enhance control over, and the uniformity of the force exerted by the clip member on the assembly components.

In accordance with a further feature of the cell concentrator, the chamber has a notch therein which exposes a portion of the slide. The notch permits the slide to be grasped during disassembly of the cell concentrator in order to minimize the risk of damaging cells sedimented to the slide.

With the above-described features, drawbacks heretofore associated with interposing a bibulous pad between a sample chamber and a slide are reduced. In particular, the features of the present embodiment combine to provide precise component alignment and simple assembly and disassembly requirements. The resulting precise component alignment reduces the incidence of cells being absorbed by the bibulous pad and thus, lost to analysis, and further reduces possible contamination of deposited cells by an imprecisely located pad. The simple disassembly of the cell concentrator decreases the risk of damage to deposited cells. Additionally the features of the present embodiment advantageously increase the degree of control over fluid absorption by the bibulous pad, both generally and more specifically by increasing the uniformity of the force applied to the pad.

As in the case of the cell concentrator embodiments described above, the rotor is adapted to receive two or four of the cell concentrators of the present embodiment in an unrestrained manner, thereby enhancing the ease of use of the apparatus. Moreover, the cell concentrator chamber of the present embodiment is shaped to rest stably on a planar surface in a tilted manner, with a front edge and a bottom edge of the chamber contacting the planar surface. With this arrangement, sample fluid in the tube is kept away from the fluid expulsion aperture, bibulous paper and adjacent slide both before and after centrifugation.

BRIEF DESCRIPTION OF THE DRAWINGS

The foregoing features of this invention, as well as the invention itself, may be more fully understood from the following detailed description of the invention in which:

FIGS. 12, 12A and 12B are views of a backing plate for use with the chamber of FIG. 10;

FIGS. 13, 13A and 13B are views of a fastener for use with the chamber of FIG. 10;

DESCRIPTION OF THE PREFERRED EMBODIMENT

Figure 1:
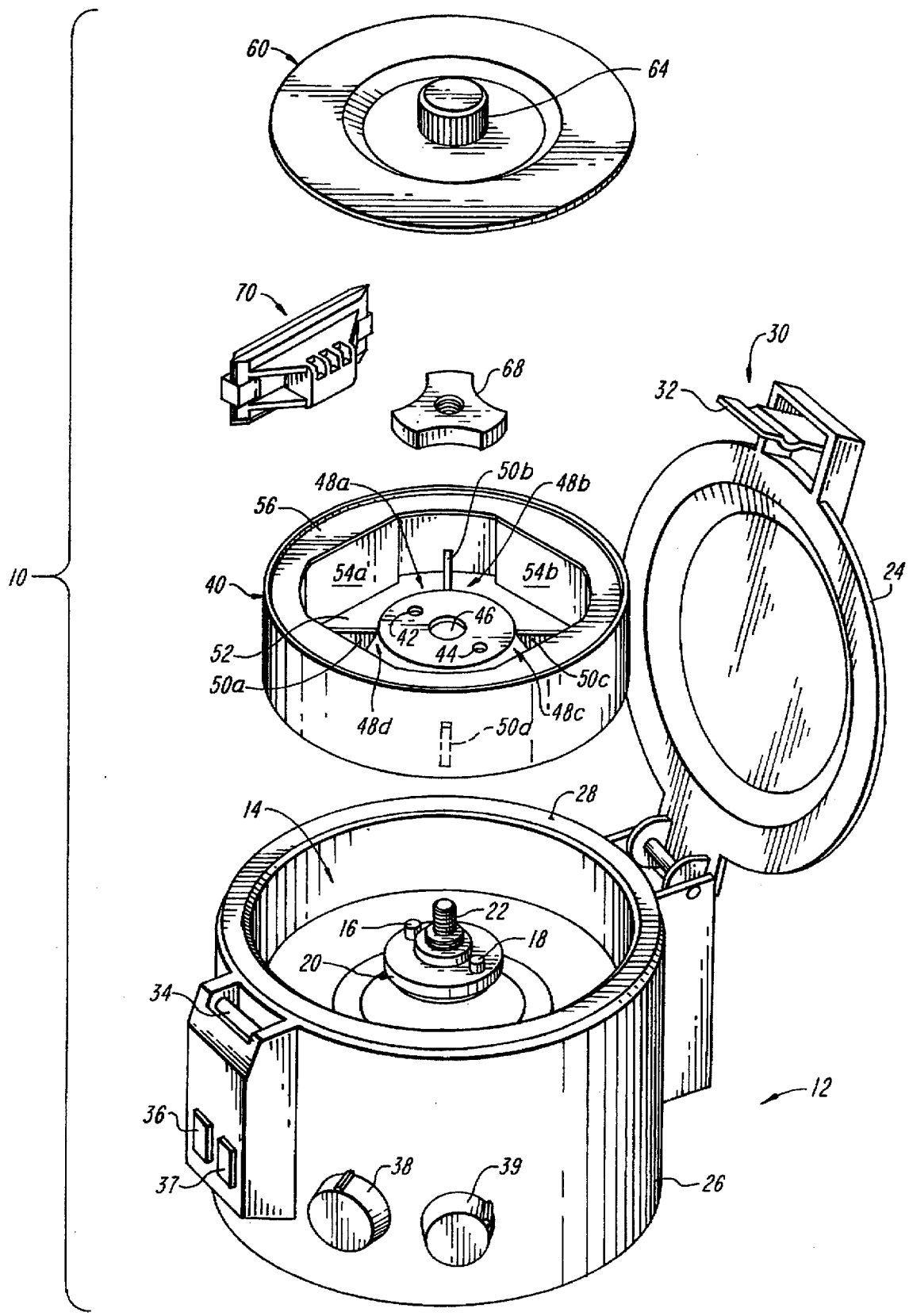
FIG. 1 is an exploded isometric view of centrifuge apparatus in accordance with the present invention.

Referring to FIG. 1, an exploded view of centrifugation apparatus 10 is shown to include an electromechanical spinner 12, a rotor 40, and a cytology cell concentrator 70. The spinner 12 supports the rotor 40 for rotation. Two or four cell concentrators (only an exemplary one 70 of which is shown and described for simplicity) are positioned in the rotor 40 for rotation therewith. The concentrator 70 is adapted to receive a fluid specimen for centrifugation. Exemplary specimens are carrier fluids having cells suspended therein and include normal body fluids such as synovial or cerebrospinal fluid, abnormal fluids such as ascites resulting from a cancer, and artificial fluids such as cell cultures.

The spinner 12 includes a housing 26 having a central depression, or bowl 14 for removably supporting the rotor 40 for rotation. More particularly, a rotor mount 20 is centrally located in the spinner bowl 14 for mounting the rotor 40. The rotor mount 20 has a vertically extending threaded shaft 22 coupled to a motor 19 (shown schematically in FIGS. 6 and 7) for rotation. The rotor 40 includes a pair of indexing holes 42, 44 for engaging complementary indexing pins 16, 18 extending upward from the rotor mount 20. The spinner shaft 22 extends through a central aperture 46 of the rotor 40. The rotor 40 is secured to the spinner 12 with a threaded rotor hold-down nut 68 which engages the threaded shaft 22.

A lid 24 is provided to cover the bowl 14 and the rotor 40 contained therein. A seal for the spinner bowl 14 is provided by a gasket 28 disposed around the perimeter of the bowl 14 and compressed by the lid 24 in closure. A latch mechanism 30 is provided to securely latch the lid 24 in a closed position over the spinner bowl 14 and includes a latch lever 32 coupled to the lid 24 and a latch pin 34 coupled to the spinner housing 26. The latch mechanism 30 is operable for manual latching and unlatching of the lid 24 and also includes an electrically operable automatic lock feature for preventing operation of the centrifuge 10 when the lid 24 is not completely closed and latched and for preventing the lid 24 from being opened during centrifugation.

The spinner 12 has several conventional controls including a start button 36 which initiates a pre-timed centrifugation cycle at a pre-selected speed and a stop button 37 which interrupts the cycle by stopping centrifugation and releasing the latch mechanism 30. Additional controls include a time selector 38 for selecting the duration of centrifugation and a speed selector 39 for selecting the speed of rotation, such as between approximately 1000 and 5000 rpm. The illustrative spinner 12 has a height of approximately five inches, a diameter of approximately seven inches, and a weight of less than approximately four pounds.

The rotor 40 has a plurality of positions 48a–d, each adapted for receiving a cell concentrator, like exemplary concentrator 70. In the illustrative embodiment described herein, the rotor 40 has four positions 48a–d for receiving up to four concentrators. More particularly, the plurality of rotor positions 48a–d are defined by a plurality of ridges, or vertical separating walls 50a–d which separate adjacent positions 48a–d. Each position 48a–d is additionally bordered by a slanted sidewall of a raised central portion 58 of the rotor 40 (FIGS. 6 and 7) and an inner sidewall 54a–d of the rotor 40.

As will be described, the cell concentrators, like exemplary concentrator 70, are shaped to rest stably on a planar surface, such as the bottom surface 52 of the rotor 40, in an advantageous tilted position. Suffice it here to say that each cell concentrator 70 is placed unrestrained in one of the rotor positions 48a–d in the resting, tilted position. When the rotor 40 is rotated, the cell concentrator 70 is forced to pivot to a vertical orientation in which the concentrator 70 contacts the adjacent inner sidewall 54a–d (only two of which 54a, b are shown in the view of FIG. 1). Upon termination of rotation, the concentrator 70 pivots back to the resting, tilted position.

A cover 60 is provided for covering the rotor 40 and rests on a top ledge 56 of the rotor 40 around the perimeter thereof. The cover 60 has a central aperture through which the spinner shaft 22 extends. A threaded nut 64 is provided to engage the threaded spinner shaft 22 and hold the cover 60 in secure position over the rotor 40. The ledge 56 has a layer of compressible material 66 disposed thereover (FIGS. 6 and 7) so that when the cover 60 is in place and the nut 64 is tightened, the compressible layer 66 is somewhat compressed in order to provide an effective seal for the rotor 40.

The ledge 56 and cover 60 prevent the formation of potentially harmful aerosols. More particularly, even if the cell concentrator 70 is overfilled with a fluid specimen, the excess fluid will leave the concentrator 70 as soon as the concentrator begins to pivot to the vertical position and while the rotor 40 is still rotating at a relatively slow speed. Such fluid will flow to the proximal inner sidewall 54a–d of the rotor 40 and be trapped under the top ledge 56. With this arrangement, the formation of potentially harmful aerosols, such as may occur when such fluid is flung at a relatively high speed onto a distant surface, is prevented.

Figure 2:
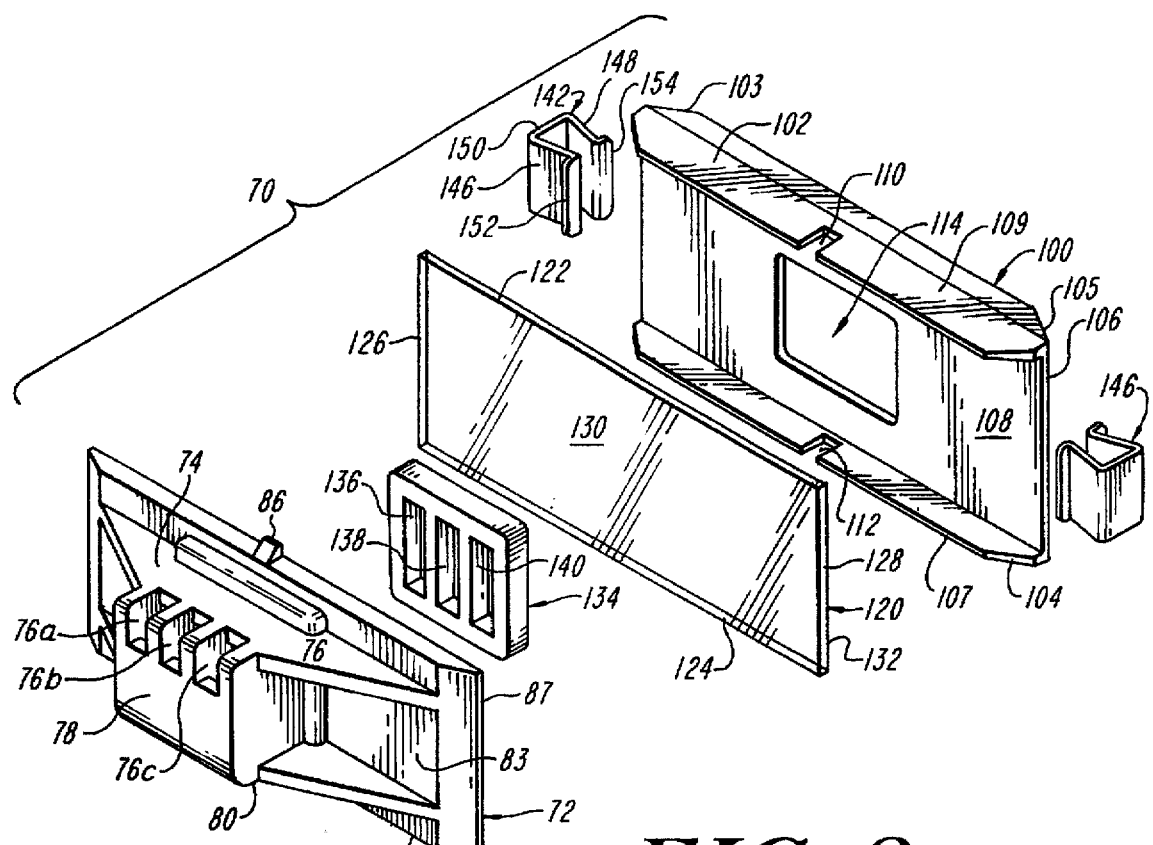
FIG. 2 is an exploded isometric view of the exemplary cytology cell concentrator assembly of FIG. 1.
Figure 2A:
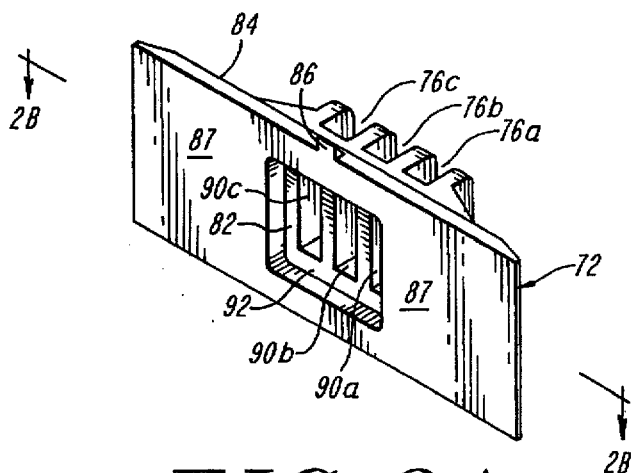
FIG. 2A is an alternate isometric view of the cell concentrator chamber of FIG. 2.
Figure 2B:
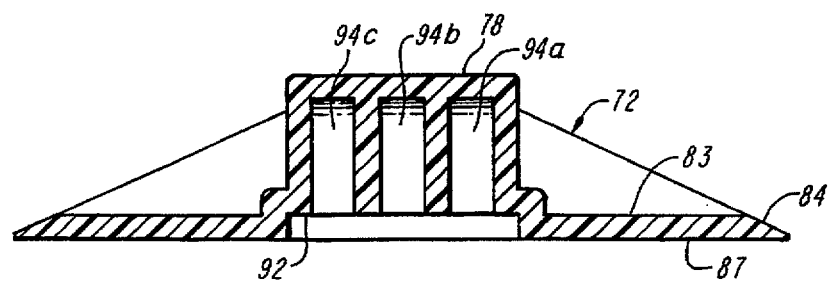
FIG. 2B is a cross-sectional view of the cell concentrator chamber of FIG. 2A.

Referring to FIGS. 2, 2A, and 2B, exemplary cell concentrator 70 is shown to include a chamber 72, a backing plate 100, a seal 134, and clips 142, 144. In assembly, a microscope slide 120 is positioned between the chamber 72 and the backing plate 100 for receiving cells from a fluid specimen during centrifugation. The slide 120 has a top edge 122, a bottom edge 124, side edges 126, 128, a front surface 130, and a rear surface 132, as shown.

The chamber 72 has a mounting flange 84 around the perimeter thereof with a front surface 87 (FIG. 2A) and a rear surface 83. A locator tab 86 protrudes from the top of the mounting flange 84, as shown, for aligning the chamber 72 with the backing plate 100, as will be described. Extending from the mounting flange 84 is a top chamber surface 74 in which one or more fluid receiving apertures 76a–c are disposed, a rear chamber surface 78, and a bottom chamber surface 80. A front chamber surface 82 has one or more fluid expulsion apertures 90a–c disposed therein. Each fluid receiving aperture 78a–c and fluid expulsion aperture 90a–c pair, respectively, defines a well 94a–c of the concentrator 70. The fluid receiving apertures 76a–c additionally extend along a top portion of the rear chamber surface 78 in order to facilitate insertion of a pipette (not shown) therein for loading a fluid specimen into the desired wells 94a–c and for removing fluid therefrom by aspiration.

The fluid expulsion apertures 90a–c are centrally located in the front chamber surface 82 and are slightly depressed in the surface 82 in order to provide a ledge 92 for receiving the seal 134 in assembly. The seal 134 is comprised of an elastomeric material, such as silicone rubber, and, in assembly, provides a fluid seal between the chamber 72 and the slide 120, as will become apparent. To this end, the seal 134 has a plurality of openings 136, 138, and 140, each one corresponding to one of the wells 94a–c of the chamber 72 and being aligned with a corresponding one of the fluid expulsion apertures 90a–c, respectively. The area of the slide 120 adjacent to each seal opening 136–140 is approximately 40mm$^2$.

Each of the wells 94a–c is adapted to receive a sample volume of approximately 200 microliters. Although the wells 94a–c have an actual volumetric capacity of approximately 450 microliters (referred to as the dead volume), the 200 microliter volume is the fluid amount that can be contained without having the fluid contact the microscope slide 120 when the concentrator 70 is assembled and positioned in its tilted, resting position. The wells 94a–c are relatively shallow, with a height from the top chamber surface 74 to the bottom surface 80 of approximately 1.2 centimeters. Various materials are suitable for fabricating the chamber 72 and backing plate 100, such as plastic. Preferably, the chamber 72 is comprised of a substantially transparent, or clear, plastic to enable viewing of a sample therein. Fiber filled plastic is preferred for use in fabricating the backing plate 100 in order to provide advantageous strength characteristics. The concentrator components (i.e., the chamber 72, backing plate 100, and clips 142, 144) may be re-used after appropriate sterilization or, alternatively, may be discarded after a single use. To this end, the cell concentrator components are preferably comprised of a material capable of being sterilized by steam.

The multiple well concentrator 70 permits simultaneous processing of multiple fluid samples. For example, it may be desirable to process three different concentrations of the same cell suspension fluid in the concentrator 70. This technique allows a user who is uncertain of the cell concentration of a fluid specimen to have adequate cell coverage without requiring a preliminary assessment of cell concentration. Alternatively, it may be desirable to process the same number of cells on the three slide locations adjacent to the three fluid expulsion apertures 90a–c and to treat each of the three cell depositions with a different diagnostic staining process in order to emphasize different cell characteristics or to develop an optimum staining process.

Figure 3:
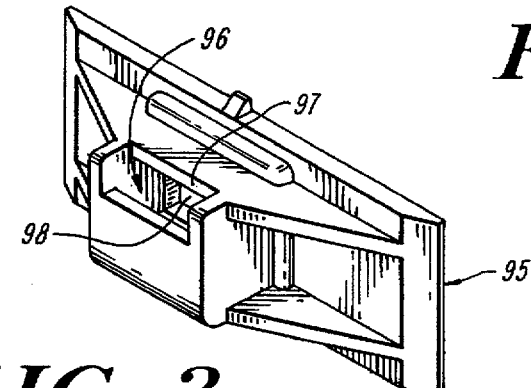
FIG. 3 is an isometric view of an alternate embodiment of the cell concentrator chamber of FIG. 2.

Referring to FIG. 3, a single well chamber embodiment 95 is shown to include analogous surfaces to the multiple well chamber 72 of FIGS. 2, 2A, and 2B but with only a single fluid receiving aperture 97 and fluid expulsion aperture 98. The dead volume of the single well 96 is approximately 1.8 milliliters and thus, its use may be desirable where larger fluid samples are to be analyzed. The single well chamber 95 is used with a fluid seal (not shown) like seal 134 of FIG. 2 but with only a single, central opening for bordering the single fluid expulsion aperture 98 in order to ensure sealed fluid communication between the well 96 and an adjacent microscope slide. The area of a slide bordered by the single well seal is approximately 200 mm$^2$.

The backing plate 100 has a protruding top edge 102, a protruding bottom edge 104, a front surface 108, and a rear surface 106, as shown in FIG. 2. Rear portions 103, 105 of the top and bottom backing plate edges 102, 104 are chamfered. Front portions 107, 109 of the top and bottom backing plate edges 102, 104 are beveled to permit the plate 100 to rest stably on a planar surface in a tilted position. The top and bottom backing plate edges 102, 104 provide vertical alignment the slide 120 and chamber 72 in assembly. Locating notches 110, 112, complementary to the locator tab 86 of the chamber 72, are provided in the top and bottom backing plate edges 102, 104 to permit dual orientation mating of the chamber 72 with backing plate 100. The notch and tab arrangement prevents the chamber 72 from sliding relative to the backing plate 100 in disassembly. Since either the top or bottom edge 102, 104 may be the "operational bottom edge" (i.e., placed on the bottom rotor surface 52), both such surfaces 102, 104 have front beveled portions 107, 109 to ensure the tilted concentrator orientation regardless of the orientation of the backing plate 100. Also provided is a viewing aperture 114 in the backing plate 100 which permits viewing of cells deposited on the slide 120 during processing, as will be discussed.

A securing mechanism, including clips 142, 144, is provided for securing, or clamping the backing plate 100 to the chamber 72, with the slide 120 sandwiched therebetween. Each of the clips 142, 144 has a pair of opposing, resilient arms 146, 148 (as labelled on exemplary clip 142) spaced by an edge 150. Flared end portions 152, 154 of each of the resilient arms 146, 148 are provided for facilitating removal of the clips during disassembly of the concentrator 70. It is noted that while the chamber 72, the backing plate 100, and the securing clips 142, 144 are shown to be separate components, one or more of these components may be integrally fabricated.

Figure 4:
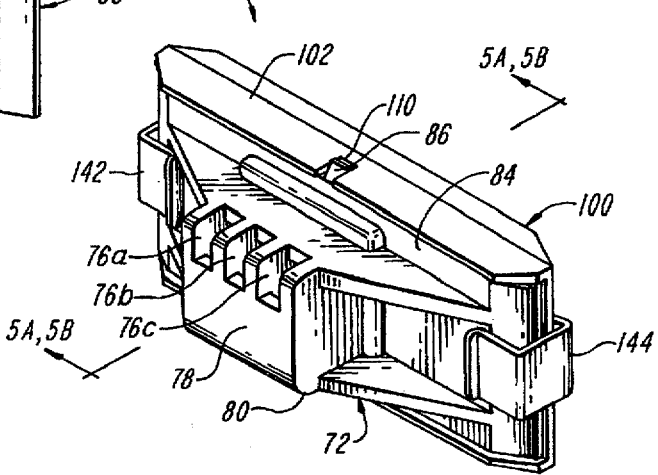
FIG. 4 is an isometric view of the assembled cell concentrator assembly of FIG. 2.

Referring also to FIG. 4, in assembly of the concentrator 70, the slide 120 is positioned on the backing plate 100 so that the rear surface 132 of the slide 120 is adjacent to the front backing plate surface 108 with the protruding top and bottom backing plate edges 102, 104, covering the top and bottom slide edges 122, 124, respectively. The chamber 72, with the seal 134 disposed on the ledge 92, is positioned over the backing plate 100 and slide 120 with the chamber tab 86 located in one of the backing plate notches 110, 112. Thereafter, slight pressure is applied to hold the chamber 72 and the backing plate 100 together as the clips 142, 144 are pushed over the ends of the concentrator assembly 70. Specifically, in assembly, a first one 146 of the resilient arms 146, 148 of each clip 142, 144 contacts an edge portion of the rear surface 83 of the mounting flange 84 and a second one 148 of the resilient arms 146, 148 contacts the rear backing plate surface 106.

Figure 5A:
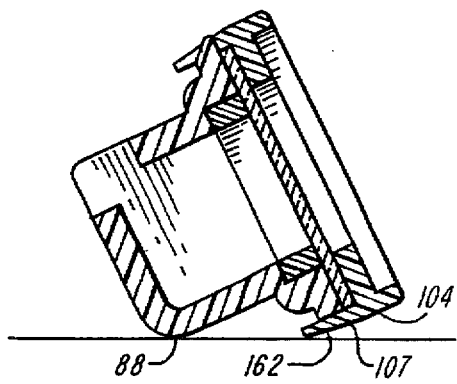
FIG. 5A is a cross-sectional view of the assembled cell concentrator assembly of FIG. 4.
Figure 5B:
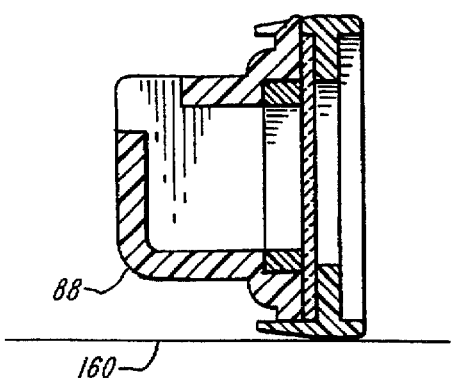
FIG. 5B is an alternate cross-sectional view of the assembled cell concentrator assembly of FIG. 4.

Referring to FIGS. 5A and 5B, cross-sectional views of the assembled concentrator 70 of FIG. 4 are shown. Specifically, FIG. 5A shows the concentrator 70 positioned in a tilted, resting position over a planar surface 160 due to the beveled front portion 107 of the backing plate edge 104. The concentrator 70 rests stably in this position with an edge 88 of the chamber 72 between the rear chamber surface 78 and the bottom chamber surface 80 (FIG. 2) and a front portion 162 of the bottom backing plate edge 104 in contact with the surface 160.

With this arrangement, the concentrator 70 is stable in the tilted position of FIG. 5A when positioned on a planar surface (i.e., such as a laboratory table or the bottom surface 52 of the rotor 40) for transfer of a fluid specimen into the wells 94a–c. The tilt of the concentrator 70 causes the fluid to be kept away from the front chamber surface 82 by gravity, thereby also keeping such fluid away from the slide 120. Preventing the fluid from contacting the slide 120 prior to centrifugation improves the uniformity of the resulting cell deposition.

During centrifugation, the concentrator 70 is centrifugally forced to pivot to the vertical position shown in FIG. 5B. In this position, centrifugal forces on the fluid causes the fluid to be expelled through the fluid expulsion apertures 90a–c onto the slide 120 for deposition of the cells suspended therein.

Figure 6:
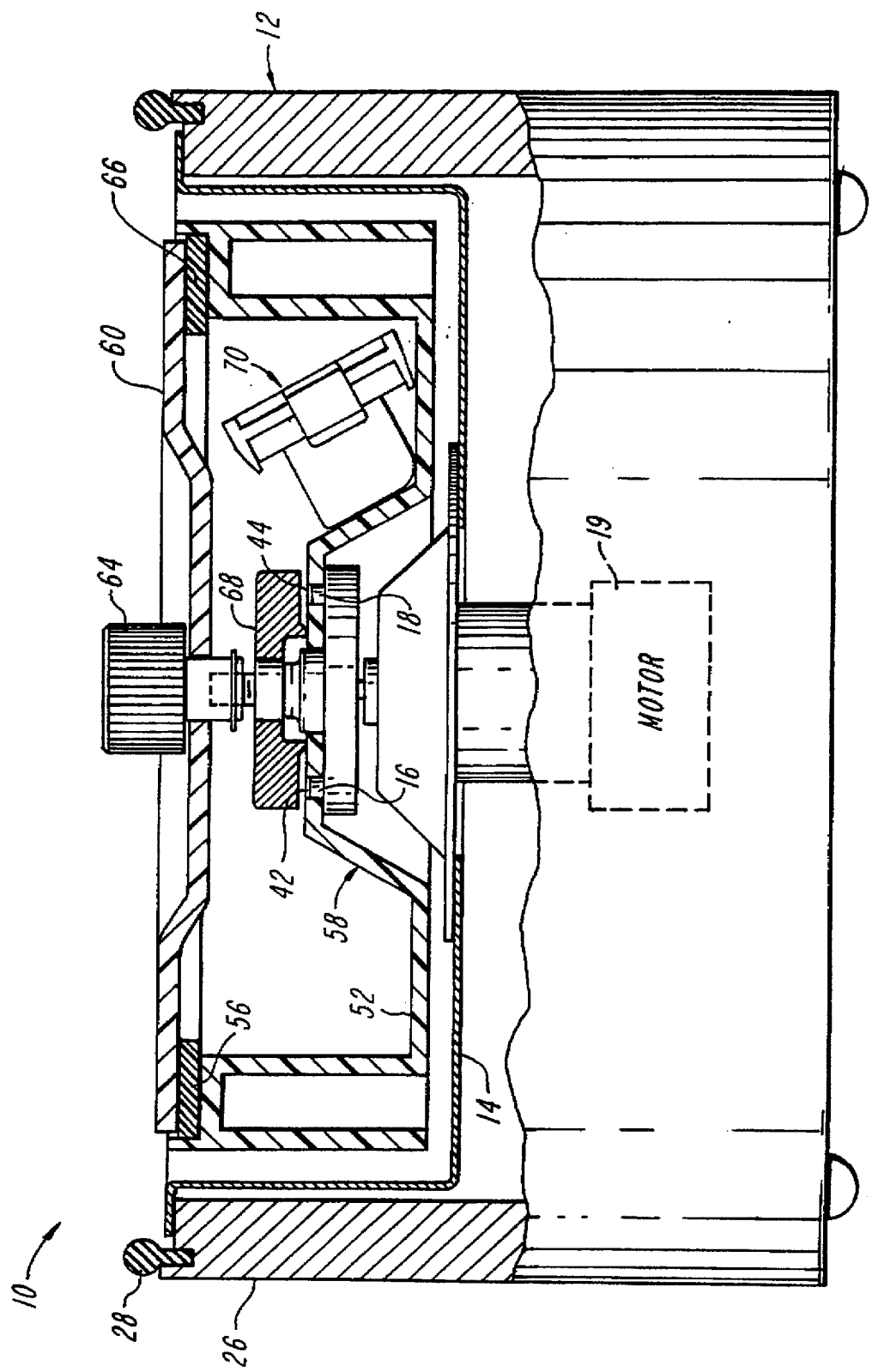
FIG. 6 is a cross-sectional view of the cytology centrifuge apparatus of FIG. 1 prior to centrifugation.

Referring to FIG. 6, a cross-sectional view of the spinner 12 is shown with the rotor 14 positioned therein. Although only exemplary concentrator 70 is shown in the rotor 40 in FIGS. 6 and 7, it is desirable to balance the rotor 40 by rotating an even number of concentrators, with concentrators having like chambers positioned opposite each other. Generally, the concentrators are placed in the rotor 40 after having specimen fluids inserted therein. In certain applications where there may be a biohazard, it may be desirable to transfer the specimens to the concentrators 70 in a safety cabinet. In fact, the entire spinner 12 may be moved to such a safety environment for loading specimens into the concentrators and placement of the concentrators in the rotor 40 due to the low weight and small size of the spinner unit 12.

As previously mentioned, the concentrators are placed in the rotor 40 in their resting, tilted position. The separating walls 50a–d of the rotor and the slanted sidewalls of the central raised portion 58 of the rotor prevent inadvertent tipping over of the concentrators, such as may occur when medical personnel load sample fluids into the concentrators or aspirate fluids therefrom. In this position, a sample fluid may be transferred into each of the desired wells 94a–c by inserting a pipette containing the sample through the fluid receiving apertures 76a–c, respectively. The tilting of the concentrators advantageously keeps the fluid away from the adjacent slide.

Figure 7:
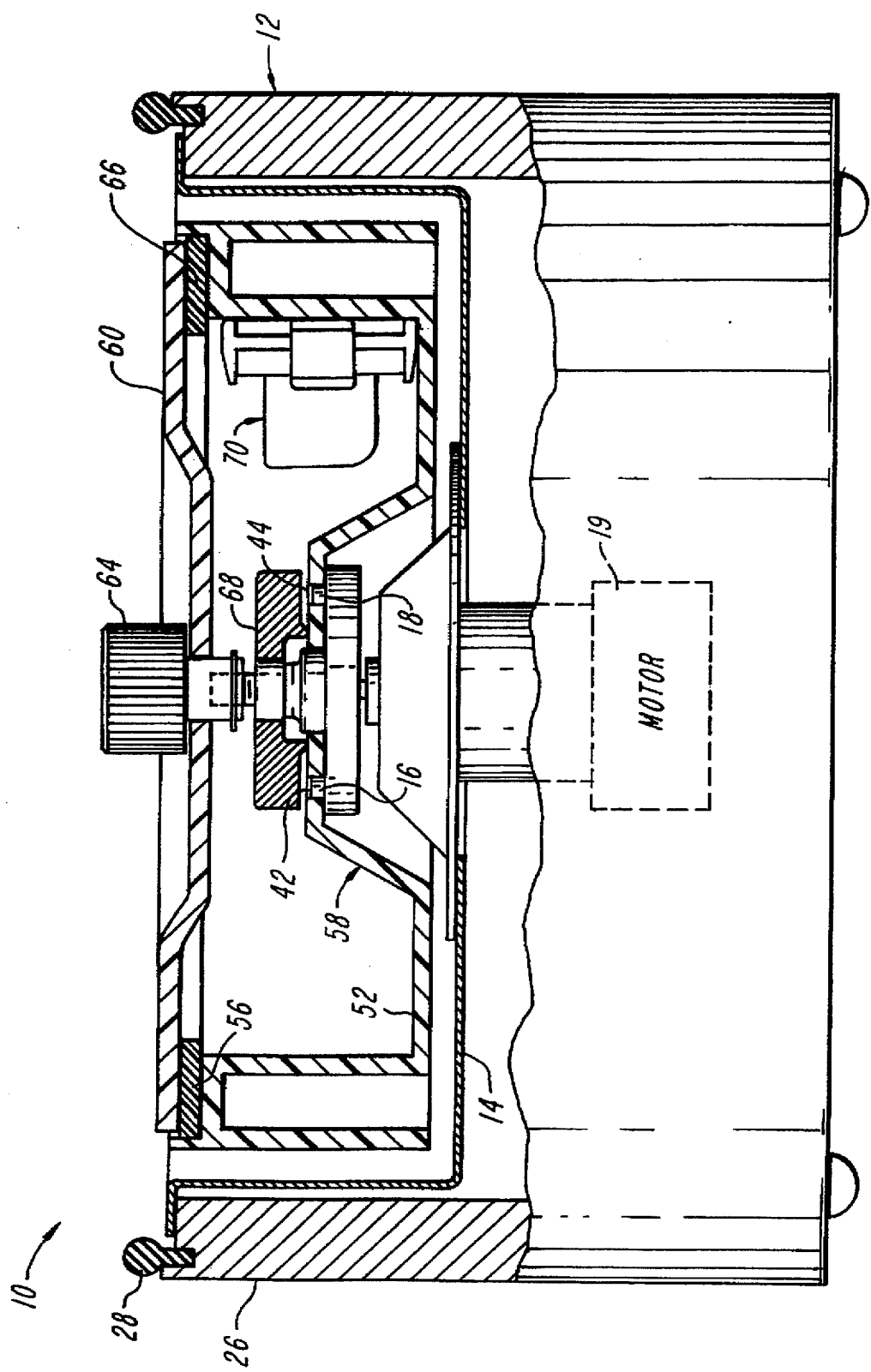
FIG. 7 is a cross-sectional view of the cytology centrifuge apparatus of FIG. 1 during centrifugation.

Referring to FIG. 7, when the spinner 12 is activated and the shaft 22 is rotated by the motor 19, concomitant rotation is imparted to the rotor 40 and the concentrators contained therein. The centrifugal force causes the concentrator 70 to pivot to the vertical orientation shown so that the backing plate 100 contacts the corresponding rotor inner sidewall 54a–d. In this position, the fluid contained in the wells 94a–c is expelled through the fluid expulsion apertures 90a–c, respectively, and onto the slide 120 to which suspended cells attach.

Once rotation of the rotor 40 is terminated, the cell concentrator 70 returns to the tilted position (shown in FIG. 6). That is, the cessation of rotation causes the concentrator 70 to automatically pivot back to the tilted position because of the beveled front portion 107 of the backing plate edge 104. Carrier fluid may be removed by aspiration with a pipette inserted through the fluid receiving apertures 76a–c. Both the insertion of specimen fluids into the wells 94a–c and aspiration of carrier fluid therefrom is facilitated by the preferred clear plastic construction of the chamber 72 which permits viewing of the fluid loading and unloading process. Other features of the concentrator 70 which facilitate loading and/or unloading fluid specimens include the shallowness of the wells 94a–c and the automatic return of the concentrator to the tilted position after centrifugation. That is, since the concentrator is tilted after centrifugation, with the carrier fluid kept away from the slide 120, a pipette inserted to remove the carrier fluid will not interfere with the deposited cells.

Once carrier fluid is removed, the deposited or sedimented cells may be stained in the still assembled concentrator 70 by any of various fixing and staining procedures.

Or, when the cell concentration of the sample fluid is very low, additional aliquots of the specimen can be added and reprocessed, or respun, to increase the number of cells on the slide 130. When the concentrator 70 is used as a staining chamber, staining reagents may be inserted into the wells 94a–c through the fluid receiving apertures 76a–c and brought into contact with the deposited cells by inverting the concentrator 70 so that so that the slide is resting in a horizontal orientation. With the concentrator 70 in this position, the reagents flow through the corresponding fluid expulsion apertures 90a–c, respectively, to contact and flow onto the slide 120. The concentrator 70 is effective as a staining chamber since there is no bibulous paper disposed between the chamber and the slide which would absorb the expensive staining reagents. Features of the concentrator 70 which enhance its use as a staining chamber include the shallowness and small volume capacity of the wells 94a–c which prevent waste of expensive staining reagents. Moreover, use of the concentrator for staining minimizes reagent waste due to evaporation since the wells 94a–c are substantially closed.

The deposited cells may be analyzed under a microscope during the staining process without disassembling the concentrator 70 through the viewing aperture 114 of the backing plate 100. More particularly, the concentrator 70 may be inverted with the rear well surface 78 placed on a microscope stage in order to view the sedimented and attached cells through the viewing aperture 114 and from the rear surface 132 of the slide 120. Alternatively, an inverted microscope may be utilized in which the objective lens is below the stage, thereby eliminating the need to invert the concentrator 70. Thus, with an inverted microscope, the concentrator 70 can be placed on the stage with the backing plate 100 down. Viewing the deposited cells during the staining process is advantageous in the development and perfection of optimum staining processes. Note that alternatively, the backing plate 100 may be comprised of a transparent material and the cells viewed through the transparent backing plate, without providing a window therein.

Figure 8A:
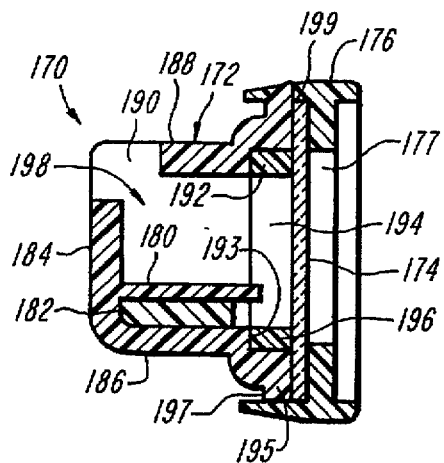
FIGS. 8A–8D are cross-sectional views of an alternate embodiment of the cell concentrator assembly of FIG. 2 at various stages of centrifugation.

Referring to FIG. 8A, an alternate embodiment 170 of the concentrator 70 is shown to include like components assembled in the manner described above in conjunction with concentrator 70. More particularly, the concentrator 170 includes a chamber 172 having at least one well 198, a slide 174, a backing plate 176 with a viewing aperture 177, and clips (not shown) for securing the chamber 172 to the backing plate 176. The chamber 172 has surfaces analogous to those of chamber 72 (FIG. 2) providing the same advantages described above in conjunction with the resting, tilted position of the concentrator 70. More particularly, the chamber 172 has a mounting flange 195 having a front surface 199 and a rear surface 197. Extending from the mounting flange 195 is a bottom chamber surface 186, a top chamber surface 188 in which at least one fluid receiving aperture 190 is disposed, and a rear chamber surface 184. A front chamber surface 193 has at least one fluid expulsion aperture 194 disposed therein in a depressed manner to provide a ledge 192 for receiving a fluid seal 196, like the seal 134 described above.

The concentrator 170 additionally includes an internal shelf 180 extending from the rear chamber surface 184 partially toward the front chamber surface 193 and the front surface of the slide 174, as shown. Also provided is a layer of bibulous paper, or a bibulous pad 182, disposed below the shelf 180 on the bottom of the chamber 172. The bibulous pad 182 is provided to absorb carrier fluid so that aspiration of fluid after centrifugation can be avoided.

Figure 8B:
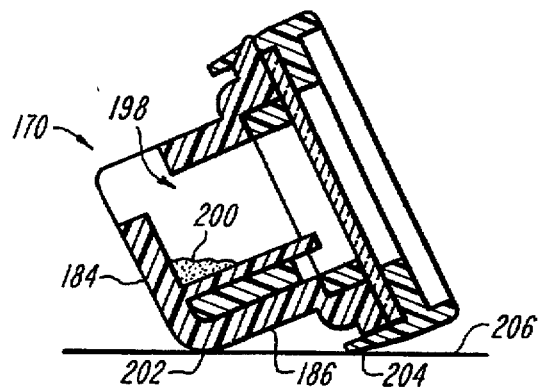

Referring to FIG. 8B, the concentrator 170 is shown in its resting, tilted position in which an edge 202 of the chamber 170 between the rear surface 184 and the bottom surface 186 and a front portion 204 of the bottom backing plate edge 176 contact the planar surface 206, in the manner described above in conjunction with FIG. 5B. A fluid sample 200 is disposed in the well 198 and, due to the tilted position of the concentrator 170, is kept away from the front chamber surface 193, as discussed above.

Figure 8C:
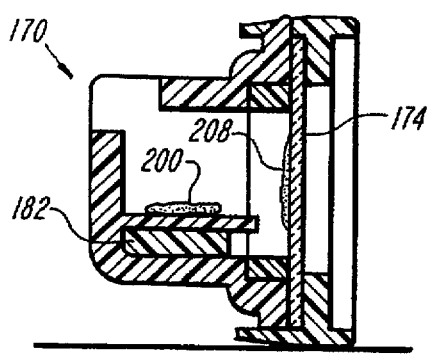
Figure 8D:
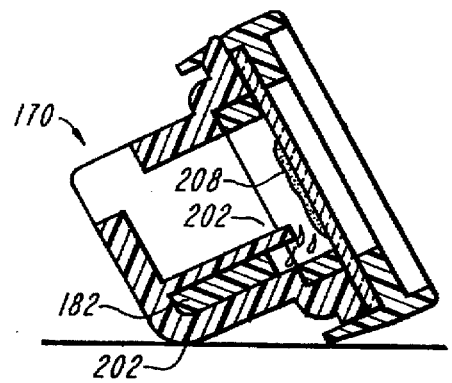

During centrifugation, the concentrator 170 pivots to the vertical position shown in FIG. 8C and cells 208 suspended in the fluid 200 are deposited on the slide 174 as the carrier fluid 200 is propelled toward and held against the slide. After rotation has terminated, the concentrator 170 returns to its resting, tilted position, as shown in FIG. 8D. As the concentrator 170 pivots back toward the tilting position, carrier fluid 200 flows down the slide 174 and towards the chamber edge 202, as shown. As the carrier fluid flows under the shelf 180, it contacts and is absorbed by the bibulous pad 182. With the shelf 180 and bibulous pad 182 described above, aspiration of carrier fluid is avoided. Moreover, the potential drawbacks typically associated with the use of bibulous paper are eliminated. More particularly, since the bibulous pad 182 is not disposed between the chamber 172 and the slide 174 as in conventional arrangements, compression of the pad is not required to control the rate and capacity of fluid absorption. Additionally, since the bibulous pad 182 is not in, or adjacent to the path of the fluid as it is forced against the slide, potential problems including premature carrier fluid absorption, loss of cells to the bibulous pad, and contamination of the deposited cells by filaments of the bibulous pad are avoided.

Figure 9:
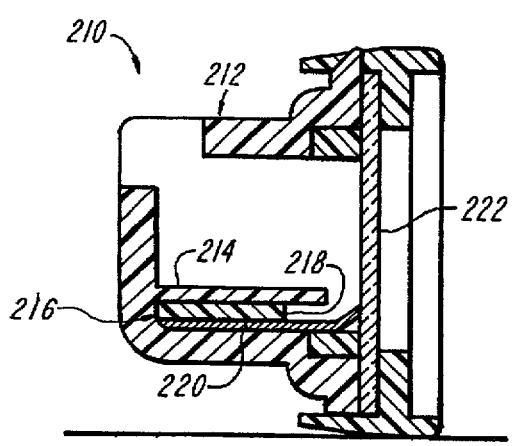
FIG. 9 is a cross-sectional view of a further alternate embodiment of the cell concentrator assembly of FIG. 2.

Referring to FIG. 9, a further alternate embodiment 210 of the cell concentrator is shown to include like components and surfaces to concentrator 170 of FIGS. 8A–D. More particularly, the chamber 212 of the concentrator 210 includes an internal shelf 214 like shelf 180 described above. Disposed under shelf 214 is a bibulous pad 216 comprised of a first bibulous pad portion 218 having a first relatively high fluid absorbing capacity and a second portion 220 having a second lower fluid absorbing capacity, preferably significantly lower than the first fluid absorbing capacity to serve as a wick.

More particularly, the higher absorbency pad portion 218 is disposed under the shelf 214. The second, lower absorbency portion 220 extends from the first portion 218 toward the slide 222 and may contact the slide 222, as shown. With this arrangement, the lower absorbency portion 220 provides wicking of carrier fluid causing such fluid to be absorbed relatively slowly and transferred to the bibulous pad. The higher absorbency pad portion 218 on the other hand quickly absorbs a larger amount of fluid than the second portion 220.

The concentrator 210 is disposed in the same positions as shown in FIGS. 8B–D prior to centrifugation, during centrifugation, and after centrifugation, respectively. Thus, although the lower absorbency portion 220 is in contact with the slide 222, absorption of carrier fluid thereby is prevented prior to centrifugation by the tilted position of the concentrator 210, as shown in FIG. 8B for concentrator 170. As soon as the rotor is rotated and the carrier fluid is forced toward and held against the slide 222, the lower absorbency portion 220 begins to draw fluid from the slide 222 toward the higher absorbency pad portion 218. Because of the relatively slow rate of absorption of the wicking portion 220 and its position at the bottom of the slide area in fluid communication with the chamber 212, premature absorption of carrier fluid and cells is avoided. Moreover, like the bibulous pad 182 of the embodiment of FIGS. 8A–D, compression of the pad in order to control the rate and capacity of fluid absorption is unnecessary since the wicking rate is controlled by the composition of the wick portion 220. Thus, this arrangement, like that of FIGS. 8A–D, eliminates the need for the user to evacuate carrier fluid from the chamber prior to further processing without disadvantageously absorbing significant fluid prior to successful deposition of the cells.

Figure 10:
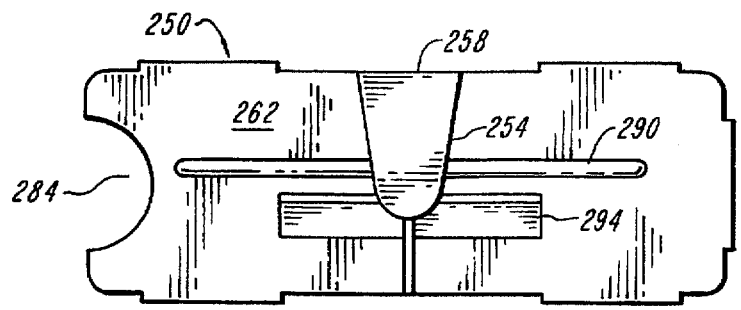
FIGS. 10, 10A and 10B are views of an alternate embodiment of a sample chamber for use with an alternate cell concentrator embodiment.
Figure 10A:
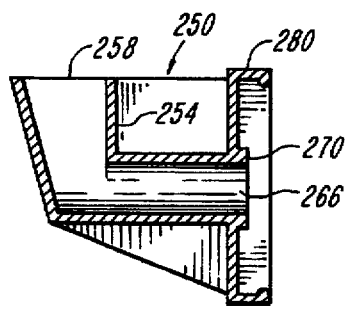
Figure 10B:
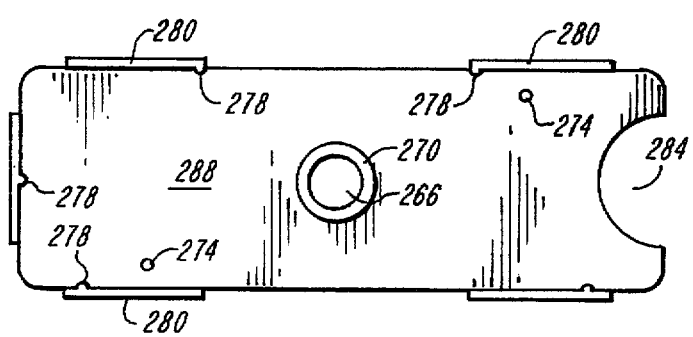
Figure 11:
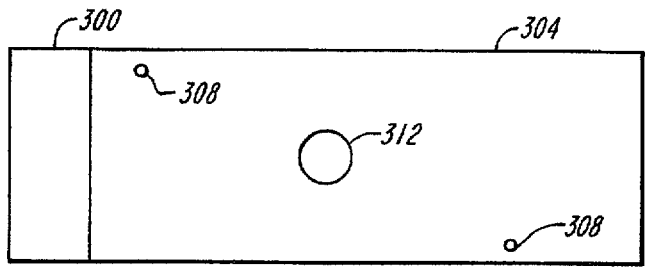
FIGS. 11, 11A and 11B are views of a slide and bibulous pad for use with the chamber of FIG. 10.
Figure 14:
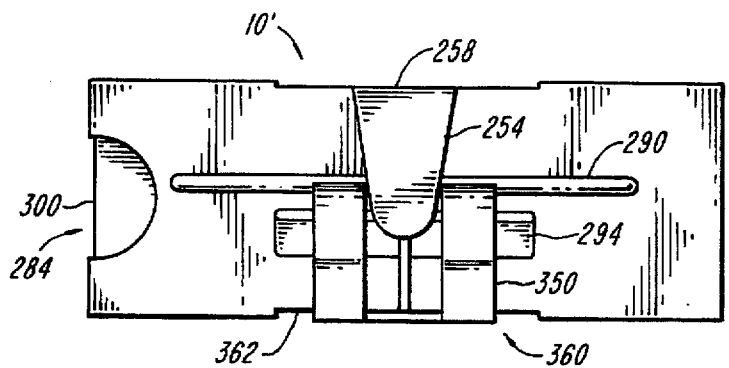
FIGS. 14, 14A and 14B are views of a cell concentrator assembly incorporating the chamber of FIG. 10, the slide and bibulous pad of FIG. 11, the backing plate of FIG. 12 and the fastener of FIG. 13.
Figure 14A:
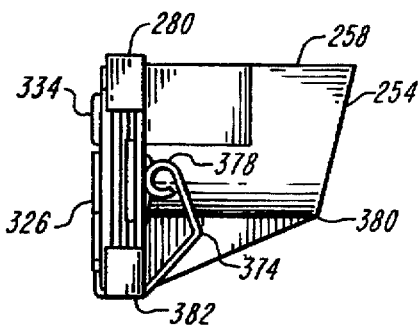
Figure 14B:
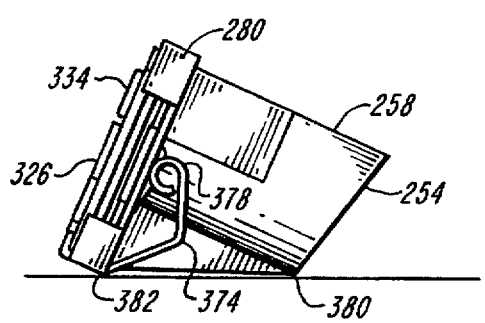

FIGS. 10–13B show various views of components associated with an alternate embodiment of a cell concentrator assembly 10' (FIGS. 14, 14A and 14B). Specifically, FIG. 10 shows a front view of the sample carrier, or chamber 250, FIG. 11 shows a front view of a slide 300 covered in part by a bibulous pad 304, FIG. 12 shows a front view of a backing plate 320 and FIG. 13 shows a front view of a securing mechanism, or fastener 350. FIGS. 10A, 11A, 12A and 13A show side views of the components of respective FIGS. 10, 11, 12 and 13 and FIGS. 10B, 11B, 12B and 13B show rear views of the components of respective FIGS. 10, 11, 12 and 13. FIG. 14 shows a front view of the assembled cell concentrator assembly, 10' FIG. 14A shows a side view of the assembly of FIG. 14, and FIG. 14B shows the assembly of FIG. 14 in a tilted position corresponding to the position of the assembly 10' before and after centrifugation.

Referring to FIGS. 10, 10A and 10B, the chamber 250 has a front surface 262 and a rear surface 288. A tube 254 extending along a portion of the front chamber surface 262 has a sample entrance aperture 258 adjacent to a top edge of the chamber into which a fluid sample can be inserted. A sample exit, or expulsion aperture 266 is provided at the rear surface 288 of the chamber 250. The side view of the chamber 250 in FIG. 10A reveals that the tube 254 is substantially L-shaped with a funnel-shaped portion adjacent to the sample entrance aperture 258 to facilitate sample loading. The sample exit aperture 266 protrudes slightly beyond the rear surface 288 of the chamber 250 in the form of an annular ring 270, as shown.

Features of the front chamber surface 262 include raised ridges 290 and 294 which protrude slightly from the front surface 262 for use in assembly, as will be described. Ridge 294 is provided in the form of a ramp, so that the extent to which it protrudes from the front surface 262 of the sample chamber 250 gradually increases as the ramp 294 approaches the ridge 290. A notch 284 is provided at an end of the chamber 250. In assembly, a portion of the slide 300 is exposed through the notch in order to facilitate removal of the slide 300 after centrifugation.

A pair of locating pins 274 protrude slightly from the rear surface 288 of the chamber 250. The chamber 250 additionally includes a plurality of locating tabs 278 extending slightly inward from a lip 280. The lip 280 extends slightly from the rear chamber surface 288 along portions of the top, side and bottom edges of the chamber 250. The lip 280 facilitates alignment of the chamber 250, slide 300, bibulous pad 304 and backing plate 320, as will be described.

Figure 11A:
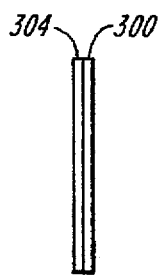
Figure 11B:
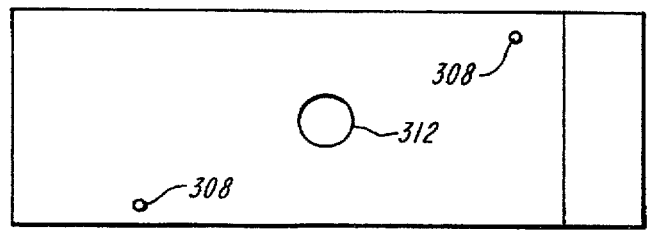

Referring also to FIGS. 11, 11A and 11B, the slide 300 is shown having a bibulous pad 304 positioned over a portion thereof. The bibulous pad 304 has a pair of locating apertures 308 which, in assembly, mate with the locating pins 274 on the rear surface 288 of the chamber 250. The bibulous pad 304 additionally includes a central aperture 312 adapted to be aligned with the annular ring 270 surrounding the fluid expulsion aperture 266 of the tube 254. In assembly, compression of the bibulous pad 304 against the annular ring 270 restricts the fluid path between the chamber 250 and the bibulous pad 304.

As shown in FIGS. 12, 12A and 12B, the backing plate 320 is a substantially planar rigid member. The backing plate 320 may be comprised of any suitable rigid material, such as metal. The backing plate 320 includes a plurality of locating notches 324 spaced along its top and bottom edges. The locating notches 324 serve to align the backing plate 320 relative to the chamber 250 in assembly, as will be described. Guide rails 326 protrude slightly from the rear surface 330 of the backing plate 320 for use in aligning the fastener 350. As will be described further below, in assembly, the slide 300 is urged against the backing plate 320. Use of the substantially planar backing plate 320 advantageously simplifies the assembly 10' and eases disassembly, thereby reducing the risk of damaging cells sedimented to the slide in the process.

Also protruding slightly from the rear surface 330 of the backing plate 320 are a plurality of stand-offs 334, as shown. During centrifugation, when the assembly 10' is forced against an adjacent wall of the rotor, the stand-offs 334 contact such adjacent wall and serve to maintain vertical orientation of the assembly. An aperture 338 through the backing plate 320 permits alignment of the bibulous pad 304 to be verified in assembly and, further, permits viewing of the sample cells sedimented on the slide 300 if so desired.

The fastener 350 shown in FIGS. 13, 13A and 13B is a substantially U-shaped clip member, including a pair of spaced legs 352 and 354 on a first side, a base portion 370 on a second side and a rear wall 358 on a third side. The legs 352, 354 are attached to the rear wall 358 by the base portion 370, as is apparent from FIG. 13A. Each of the fastener legs 352, 254 has an outwardly extending jog (labelled 374 in FIG. 13A) and a rounded terminal end (labelled 378 in FIG. 13A).

Referring also to FIGS. 14 and 14A, in assembly, the bibulous pad 304 is aligned with the chamber 250 by positioning the locating apertures 308 of the bibulous pad 304 over the locating pins 274 on the rear surface 288 of the chamber 250. Thereafter, the slide 300 is positioned over the bibulous pad 304 and within the lip 280 of the chamber 250. A portion of the slide 300 will be visible through the notch 284. The backing plate 320 is located relative to the sub-assembled chamber 250, slide 300 and bibulous pad 304 by placing the front surface 328 of the backing plate 320 over the slide 300 and aligning the notches 324 of the backing plate 320 with the locating tabs 278 of the chamber 250.

Thereafter, the fastener 350 is positioned over the sub-assembled chamber 250, bibulous pad 304, slide 300 and backing plate 320 in order to compress the components together. This compression can be controlled or adjusted by varying the thickness of the fastener material and/or by varying the distance between the rounded terminal 378 and the rear wall 358 of the fastener 350. More particularly, the fastener 350 is directed over the bottom edge 360 of the sub-assembly, with the rear fastener wall 358 adjacent to the rear surface 330 of the backing plate 320 within the guide rails 326 and the spaced legs 352, 354 adjacent to the front surface 262 of the chamber 250. The fastener 350 is urged over the sub-assembly until the base portion 370 of the fastener contacts the bottom edge 362 of the chamber 250. In this position, the round terminal ends 378 of the fastener legs 352, 354 rest in the detent formed between ridges 290 and 294 on the front surface 262 of the chamber 250, with the fastener legs 352, 354 straddling the tube 254 (see FIG. 14). With this arrangement, the chamber 250 and the backing plate 320 are urged together with the bibulous pad 304 and slide 300 sandwiched therebetween. As noted above, the force exerted on the bibulous pad 304 and against the annular ring 270 restricts the fluid path between the chamber 250 and the bibulous pad 304.

Prior to centrifugation, the cell concentrator assembly 10' rests unrestrained in one of the rotor positions 48a–d (FIG. 1) on the floor of the rotor 40 in a tilted manner, as shown in FIG. 14B, with a front edge 380 of the chamber and a bottom edge 382 of the chamber 250 contacting the rotor floor. During centrifugation, the assembly 10' tilts to the vertical position of FIG. 14A, with the stand-offs 334 contacting an adjacent wall 54a–d of the rotor 40. As the sample fluid moves toward the slide 300, cells suspended within the sample are sedimented to the slide while excess sample fluid is absorbed by the bibulous pad 304.

Various features of the present embodiment advantageously address drawbacks heretofore associated with the use of a bibulous pad interposed between a chamber and a slide. In particular, these drawbacks are minimized by the precise alignment of the components and in particular, by the precise alignment of the bibulous pad 304 relative to the fluid expulsion aperture 266 and the verification of such alignment possible through the backing plate aperture 338. Such precise component alignment reduces the incidence of cells being absorbed by the bibulous pad and thus, lost to analysis, and further reduces possible contamination of deposited cells by an imprecisely located pad placement. Features of the cell concentrator including, inter alia, the annular ring 270, fastener 350, ridges 290 and 294 and guide rails 326 provide a higher degree of control over fluid absorption by the bibulous pad 304 than otherwise possible by increasing the uniformity of the force exerted on the pad. Furthermore, the simple assembly and disassembly techniques associated with the present embodiment decrease the risk of damage to deposited cells.

After centrifugation, the cell concentrator assembly 10' returns to its tilted position (FIG. 14B) with the front edge 380 and the bottom edge 382 of the chamber 250 contacting the rotor floor. The assembly 10' is disassembled by removal of the fastener 350. This is achieved by pushing the rounded terminal ends 378 of the fastener legs 352, 354 over the chamber ridge 294, so as to disengage the fastener 350 from the assembly 10'. The upper ridge 290 is elongated in order to facilitate such removal by providing a surface to grasp. Once the fastener 350 is removed, the remaining components may be readily separated for further processing of the slide. The portion of the slide 300 exposed through the notch 284 may be used to grasp the slide during disassembly, in order to facilitate removal of the slide without damaging cells sedimented to the slide.

Figure 15:
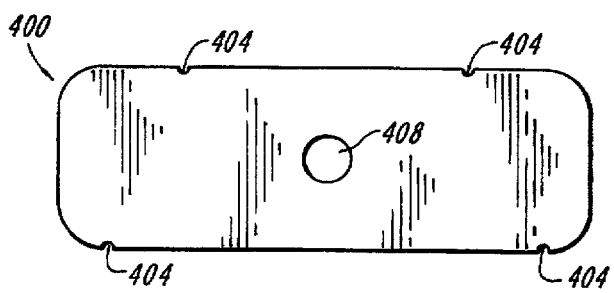
FIGS. 15, 15A and 15B are views of an alternate backing plate for use with the chamber of FIG. 10, the slide and bibulous pad of FIG. 11, the backing plate of FIG. 12 and the fastener of FIG. 13.
Figure 15A:
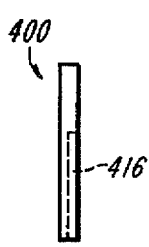
Figure 15B:
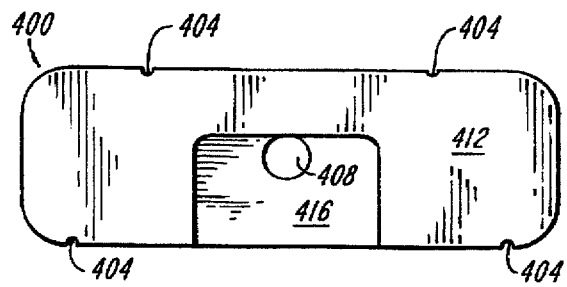

Referring also to FIGS. 15, 15A and 15B, an alternate substantially planar backing plate 400 is shown to include a plurality of locating notches 404 spaced along its top and bottom edges. The locating notches 404 serve to align the backing plate 400 relative to the chamber 250 (FIG. 10) in assembly in the manner described above. The backing plate 400 additionally includes a central aperture 408 adapted to be aligned with the aperture 312 through the bibulous pad 304 and the annular ring 270 (FIG. 10) at the terminal end of the sample exit aperture 266 in assembly. Aperture 408 permits alignment of the bibulous pad 304 to be verified in assembly and, further, permits viewing of the sample cells sedimented on the slide 300 if so desired.

The rear surface 412 of the backing plate 400 has a recess 416 therein. In assembly, when the backing plate 400 is assembled with the sample chamber 250, the bibulous pad 304 and the slide 300, the fastener 350 is positioned over the assembly, with the rear wall 358 in the recess 416. With this arrangement, the recess 416 serves the function of the guide rails 326 (FIG. 12) by aligning the fastener 350 relative to the backing plate and other components.

As is apparent from comparing FIGS. 12A and 15A, the backing plate 400 is thicker than the backing plate 320. For example, in the illustrative embodiment, the thickness of the backing plate 320 is on the order of approximately 0.04" (with the stand-offs 334 also being approximately 0.04" thick) and the thickness of the backing plate 400 is on the order of approximately 0.08". The backing plate 400 may be comprised of any suitably rigid material, such as metal or plastic. The increased thickness of backing plate 400 permits the elimination of stand-offs 334 (FIG. 12). That is, in the case of backing plate 400, the rear surface 412 of the backing plate itself contacts an adjacent wall of the rotor during centrifugation and serves to maintain vertical orientation of the assembly.

Figure 16:
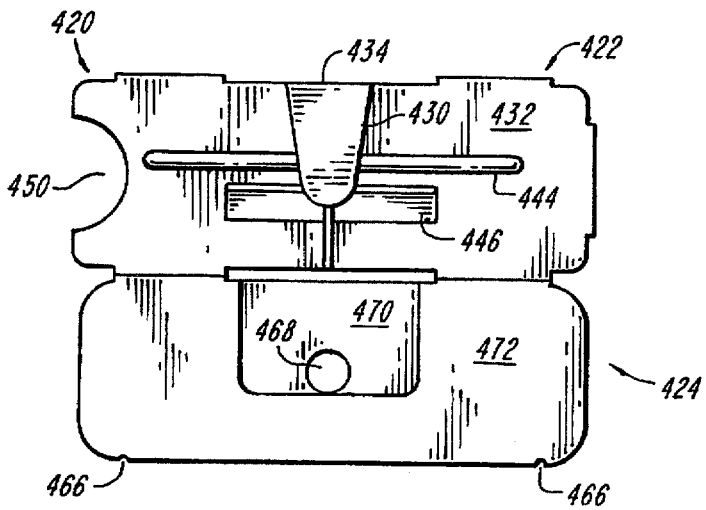
FIGS. 16, 16A and 16B are views of an alternate combination sample chamber and backing plate for use with the slide and bibulous pad of FIG. 11 and the fastener of FIG. 13.
Figure 16A:
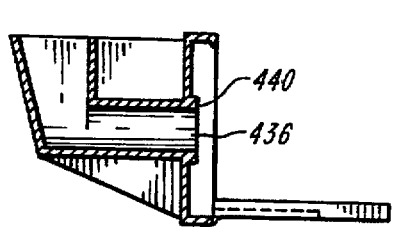
Figure 16B:
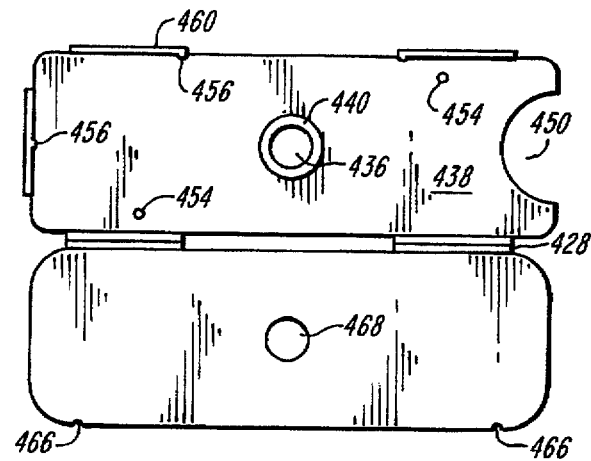

Referring to FIGS. 16, 16A and 16B, a combination sample chamber and backing plate embodiment 420 is shown. The sample chamber/backing plate combination member 420 includes a sample chamber portion 422 and a backing plate portion 424, coupled together by a living hinge 428. In the illustrative embodiment, the combination member 420 is comprised of plastic.

The sample chamber portion 422 includes several of the same features as the sample chamber 250 (FIG. 10). Specifically, the sample chamber portion 422 includes a tube 430 extending along a portion of the front surface 432, with the tube having a sample entrance aperture 434 and a sample exit aperture 436 terminating at the rear surface 438 of the chamber portion 422 in an annular ring 440. A pair of ridges 444 and 446 protrude slightly from the front surface 432 and a notch 450 is provided at an end of the chamber portion 422. A pair of locating pins 454 protrude slightly from the rear surface 438 and a plurality of locating tabs 456 extend slightly inward from a lip 460 which extends slightly from the rear chamber surface 438 along portions of the top and side edges of the chamber portion 422.

The backing plate portion 424 includes several of the same features as the backing plate 400 (FIG. 15). Specifically, the backing plate portion 424 includes a plurality of locating notches 466 spaced along its bottom edge and a central aperture 468 aligned with the annular ring 440 in assembly. A recess 470 in the rear surface 472 of the backing plate portion 424 is provided for aligning the fastener 350 in assembly.

Figure 17:
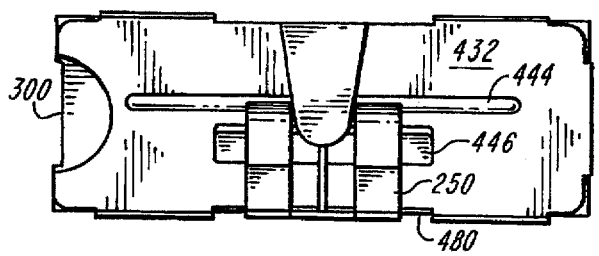
FIGS. 17 and 17A are views of a cell concentrator assembly incorporating the sample chamber/backing plate of FIG. 16, the slide and bibulous pad of FIG. 11 and the fastener of FIG. 13.
Figure 17A:
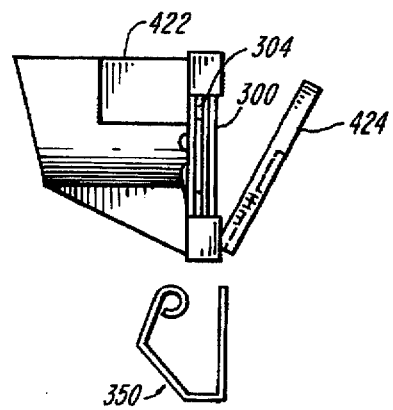

Referring also to FIGS. 17 and 17A, a cell concentrator assembly including the combination sample chamber and backing plate member 420, the slide 300, the bibulous pad 304 and the fastener 350 is shown. In assembly, a user places a microscope slide 300 over a bibulous pad 304, with both such components retained within the lip 460. The slide 300 is then covered by the hinged backing plate portion 424. The assembly is secured together by moving the fastener 350 over the hinged bottom surface of the sample chamber/ backing plate 420 until the fastener base portion 370 contacts the bottom edge 480 of the combination member 420.

Having described the preferred embodiments of the invention, it will be apparent to one of skill in the art that other embodiments incorporating their concepts may be used. Accordingly, the invention should be limited only by the spirit and scope of the appended claims.

We claim:

1. Centrifuge apparatus comprising:

a spinner;

a rotor removably supported for rotation by said spinner, said rotor having a plurality of positions; and a cell concentrator disposed in one of said plurality of positions of said rotor, said cell concentrator comprising:
   a chamber having a tube with a fluid receiving aperture in a top chamber surface for receiving a fluid specimen and a fluid expulsion aperture in a rear chamber surface;
   a slide in fluid communication with said fluid expulsion aperture of said chamber;
   a bibulous pad disposed adjacent to said slide and having an aperture aligned with said fluid expulsion aperture;
   a substantially planar backing plate against which said slide is urged in assembly; and
   a securing mechanism securing said backing plate to said chamber with said slide and said bibulous pad sandwiched therebetween, wherein said fluid expulsion aperture is bordered by a raised rim, and said bibulous pad has an aperture aligned with said fluid expulsion aperture so that, in assembly, said bibulous pad is compressed against said raised rim to restrict a fluid path between said chamber and said bibulous pad, wherein said securing mechanism comprises a clip member having a pair of legs attached to a rear wall by a base portion, wherein said rear wall of said securing mechanism contacts a rear surface of said backing plate and said pair of legs contact a front surface of said chamber, with said pair of legs straddling said tube.

2. The centrifuge apparatus recited in claim 1 wherein said chamber has a pair of ridges disposed on said front surface and each of said pair of legs of said clip member has a rounded end portion which is positioned between said pair of ridges in assembly.

3. The centrifuge apparatus recited in claim 1 wherein said chamber has a locating pin protruding from said rear chamber surface and said bibulous pad has a locating aperture mated with said locating pin of said chamber in assembly.

4. The centrifuge apparatus recited in claim 1 wherein each of said plurality of positions of said rotor has a substantially planar bottom portion and wherein said cell concentrator is disposed unrestrained on said substantially planar bottom portion of one of said plurality of positions of said rotor prior to rotation of said rotor.

5. The centrifuge apparatus recited in claim 1 wherein said cell concentrator is stable when rested in one of said positions of said rotor with a front edge of said chamber and a bottom edge of said chamber contacting a bottom surface of said rotor so that a fluid specimen in said tube is kept away from said rear chamber surface and toward said bottom rotor surface.

6. The centrifuge apparatus recited in claim 1 wherein an edge of said chamber has a notch therein exposing a portion of said slide to facilitate separation of said slide from said chamber.

7. The centrifuge apparatus recited in claim 1 wherein said chamber has a locating tab along a protruding lip thereof and said backing plate has a notch along an edge portion thereof, wherein said tab of said chamber and said notch of said backing plate are aligned in assembly and wherein said slide and said bibulous pad are bordered by said lip of said chamber in assembly.

8. The centrifuge apparatus recited in claim 1 wherein said rear chamber surface has an edge and a lip disposed along at least a portion of said edge and wherein said slide is disposed within said lip.

9. A cell concentrator comprising:
   a chamber having a tube with a fluid receiving aperture for receiving a fluid specimen and a fluid expulsion aperture;
   a slide in fluid communication with said fluid expulsion aperture of said chamber;
   a bibulous pad disposed adjacent to said slide and having an aperture aligned with said fluid expulsion aperture;
   a substantially planar backing plate against which said slide is urged in assembly; and
   a securing mechanism securing said backing plate to said chamber with said slide and said bibulous pad sandwiched therebetween, wherein said securing mechanism comprises a clip member having a pair of legs attached to a rear wall by a base portion, wherein said rear wall of said securing mechanism contacts a rear surface of said backing plate and said pair of legs contact a front surface of said chamber, with said pair of legs straddling said tube.

10. The cell concentrator recited in claim 9 wherein said chamber has a pair of ridges disposed on said front surface and each of said pair of legs of said clip member has a rounded end portion which is positioned between said pair of ridges in assembly.

11. The cell concentrator recited in claim 9 wherein said chamber has a locating pin protruding from a rear chamber surface and said bibulous pad has a locating aperture mated with said locating pin of said chamber in assembly.

12. The cell concentrator recited in claim 9 wherein an edge of said chamber has a notch therein exposing a portion of said slide to facilitate separation of said slide from said chamber.

13. The cell concentrator recited in claim 9 wherein said chamber has a locating tab along a protruding lip thereof and said backing plate has a notch along an edge portion thereof, wherein said tab of said chamber and said notch of said backing plate are aligned in assembly and wherein said slide and said bibulous pad are bordered by said lip of said chamber in assembly.

14. The centrifuge apparatus recited in claim 9 wherein said chamber has a rear chamber surface, said rear chamber surface has an edge and a lip disposed along at least a portion of said edge and wherein said slide is disposed within said lip.

15. A cell concentrator comprising:
   a chamber having a tube with a fluid entrance aperture in a top surface of said chamber and a fluid expulsion aperture terminating at an annular ring in a rear surface of said chamber, said chamber further having a protruding lip extending outward from said rear chamber surface along edge portions of said chamber and having a plurality of locating tabs thereon;
   a bibulous pad disposed adjacent to said rear surface of said chamber within said lip of said chamber;
   a slide disposed adjacent to said bibulous pad and within said lip of said chamber;
   a backing plate having a plurality of locating notches along edge portions thereof for alignment with said locating tabs of said chamber, said backing plate further having a pair of guide rails protruding from a rear surface thereof; and a clip member having a pair of legs attached to a rear wall by a base portion, wherein said rear wall of said clip member contacts said rear surface of said backing plate between said pair of guide rails and said pair of legs contact a front surface of said chamber, with said pair of legs straddling said tube.

16. The cell concentrator recited in claim 15 wherein said sample chamber and said backing plate are hinged together.

17. The cell concentrator recited in claim 15 wherein said rear surface of said chamber has a plurality of locating pins extending therefrom and said bibulous pad has a plurality of locating apertures mated with said locating pins of said chamber.

18. The cell concentrator recited in claim 15 wherein said chamber has a notch in an end thereof which exposes a portion of said slide in assembly.

19. The cell concentrator recited in claim 15 wherein said backing plate has an aperture aligned with said fluid expulsion aperture of said tube.

20. The cell concentrator recited in claim 15 wherein said backing plate has a plurality of stand-offs protruding from said rear surface thereof.

* * * * *